US011156602B2

(12) United States Patent
Ohbayashi et al.

(10) Patent No.: US 11,156,602 B2
(45) Date of Patent: Oct. 26, 2021

(54) COMBINATION PRODUCT FOR DETECTING TARGET MARKER

(71) Applicant: NICHIREI BIOSCIENCES INC., Tokyo (JP)

(72) Inventors: Hirokazu Ohbayashi, Tokyo (JP); Kayoko Fujita, Tokyo (JP)

(73) Assignee: NICHIREI BIOSCIENCES INC., Tokyo (JP)

( * ) Notice: Subject to any disclaimer, the term of this patent is extended or adjusted under 35 U.S.C. 154(b) by 124 days.

(21) Appl. No.: 16/399,050

(22) Filed: Apr. 30, 2019

(65) Prior Publication Data

US 2019/0324020 A1 Oct. 24, 2019

Related U.S. Application Data

(62) Division of application No. 15/305,461, filed as application No. PCT/JP2015/062423 on Apr. 23, 2015, now Pat. No. 10,324,084.

(30) Foreign Application Priority Data

Apr. 23, 2014 (JP) ................................. 2014-089675

(51) Int. Cl.
| | |
|---|---|
| G01N 33/58 | (2006.01) |
| G01N 33/53 | (2006.01) |
| C12Q 1/68 | (2018.01) |
| G01N 33/532 | (2006.01) |
| G01N 33/535 | (2006.01) |
| G01N 33/536 | (2006.01) |
| C12Q 1/28 | (2006.01) |
| C12Q 1/42 | (2006.01) |

(52) U.S. Cl.
CPC ........... *G01N 33/5306* (2013.01); *C12Q 1/68* (2013.01); *G01N 33/532* (2013.01); *G01N 33/535* (2013.01); *G01N 33/536* (2013.01); *G01N 33/58* (2013.01); *G01N 33/581* (2013.01); *C12Q 1/28* (2013.01); *C12Q 1/42* (2013.01)

(58) Field of Classification Search
CPC .. G01N 33/532; G01N 1/5306; G01N 33/536; G01N 33/535; G01N 33/58; G01N 33/581; G01N 33/53; G01N 33/5306; G01N 33/6857; C12Q 1/68; C12Q 1/28; C12Q 1/42
See application file for complete search history.

(56) References Cited

U.S. PATENT DOCUMENTS

| | | | |
|---|---|---|---|
| 4,657,853 | A | 4/1987 | Freytag et al. |
| 6,027,874 | A | 2/2000 | Cucurou et al. |
| 6,252,053 | B1 | 6/2001 | Ohbayashi et al. |
| 2001/0005583 | A1 | 6/2001 | Ohbayashi et al. |
| 2004/0002146 | A1 | 1/2004 | Ohbayashi et al. |
| 2005/0019573 | A1 | 1/2005 | Kai |
| 2005/0208529 | A1* | 9/2005 | Winther ........... G01N 33/54306 435/6.12 |
| 2013/0224287 | A1 | 8/2013 | Reis et al. |

FOREIGN PATENT DOCUMENTS

| | | |
|---|---|---|
| CN | 1300942 | 6/2001 |
| CN | 101833000 | 9/2010 |
| CN | 102565383 | 7/2012 |
| EP | 0 752 102 | 1/1997 |
| GB | 2 098 730 | 11/1982 |
| JP | 9-511067 | 11/1997 |
| JP | 2001-181299 | 7/2001 |
| JP | 2007-513334 | 5/2007 |
| JP | 2013-134083 | 7/2013 |
| JP | 2013-541716 | 11/2013 |
| JP | 2014-503475 | 2/2014 |
| WO | 03/031974 | 4/2003 |
| WO | 2005/054860 | 6/2005 |
| WO | 2005/075997 | 8/2005 |
| WO | 2006/070582 | 7/2006 |
| WO | 2010/094283 | 8/2010 |
| WO | 2011/096468 | 8/2011 |

(Continued)

OTHER PUBLICATIONS

Jaroslav Mokry, "Versatility of Immunohistochemical Reactions: Comprehensive Survey of Detection Systems", ACTA Medica (Hradec Kralove), 1996, vol. 39, No. 4, pp. 129-140.
Office Action dated Jul. 28, 2017 in Chinese Application No. 201580021174.9, with English Translation.
International Preliminary Report on Patentability dated Oct. 25, 2016 in corresponding International Application No. PCT/JP2015/062423.

(Continued)

*Primary Examiner* — Carmencita M Belei
(74) *Attorney, Agent, or Firm* — Wenderoth, Lind & Ponack, L.L.P.

(57) ABSTRACT

The present invention relates to a combination product for detecting a target marker simply and with high sensitivity. More specifically, the present invention relates to a combination product for detecting a target marker in a biological sample in combination with a target marker binding molecule which is capable of binding specifically to the target marker in the biological sample, the combination comprising, at least:

(a) a first binding agent comprising a first binding molecule which is capable of directly or indirectly binding specifically to the target marker binding molecule, and a labeling substance;
(b) a linker molecule which is capable of binding specifically to the first binding agent; and
(c) a second binding agent which is capable of binding specifically to the linker molecule, and comprises a second binding molecule and a labeling substance.

4 Claims, 11 Drawing Sheets

(56) References Cited

FOREIGN PATENT DOCUMENTS

| | | |
|---|---|---|
| WO | 2012/054824 | 4/2012 |
| WO | 2014/009474 | 1/2014 |
| WO | 2014/046248 | 3/2014 |

OTHER PUBLICATIONS

International Search Report dated Jul. 28, 2015 in International Application No. PCT/JP2015/062423.
Extended European Search Report dated Aug. 17, 2017 in European Patent Application No. 15783732.9.
Ramos-Vara et al., "Comparison of two polymer-based immunohistochemical detection systems: Envision+TM and ImmPRESS TM", Journal of Microscopy, vol. 224, No. 2, Nov. 1, 2006, pp. 135-139, XP055397091.
Shingo Kamoshida, Immunostaining technique from basics—How to surely stain—, Histochemistry and Cytochemistry 2012, Japan Society of Histochemistry and Cytochemistry, 2012, pp. 11-25.

* cited by examiner

| | Comparative Example 1 | Comparative Example 2 |
|---|---|---|
| First binding agent | (M)5 μg/mL + (R)5 μg/mL | (M)5 μg/mL + (R)5 μg/mL |
| Second binding agent | None | (G)7.5 μg/mL |
| p53 Gastric Cancer | | |
| CDX-2 Colorectal Cancer | | |

FIG. 2

| | Comparative Example 3 | Comparative Example 4 | Example 1 | Example 2 |
|---|---|---|---|---|
| First binding agent | (M)5 μg/mL + (R)5 μg/mL | (M)5 μg/mL + (R)5 μg/mL | (M)5 μg/mL + (R)5 μg/mL | (M)5 μg/mL + (R)5 μg/mL |
| Linker molecule | None | None | Goat anti-HRP 1 μg/mL | Goat anti-HRP 5 μg/mL |
| Second binding agent | None | (G)7.5 μg/mL | (G)7.5 μg/mL | (G)7.5 μg/mL |
| p53 Gastric Cancer | | | | |
| CDX-2 Colorectal Cancer | | | | |

FIG. 3

| | Comparative Example 5 | Example 3 | Comparative Example 6 | Example 4 | Comparative Example 7 | Example 5 |
|---|---|---|---|---|---|---|
| First binding agent | (M)5 + (R)5 | (M)5 + (R)5 | (M)5 + (R)5 | (M)5 + (R)5 | (M)5 + (R)5 | (M)5 + (R)5 |
| Linker molecule | None | Mouse anti-HRP 5 μg/mL | None | Rabbit anti-HRP 5 μg/mL | None | Goat anti-HRP 5 μg/mL |
| Second binding agent | (M)7.5 | (M)7.5 | (R)7.5 | (R)7.5 | (G)7.5 | (G)7.5 |
| p53 Gastric Cancer | | | | | | |
| CDX-2 Colorectal Cancer | | | | | | |

FIG. 4

| | Comparative Example 8 | Comparative Example 9 | Example 6 | Example 7 |
|---|---|---|---|---|
| First binding agent | Dako EnVision™ + Dual Link System-HRP | Dako EnVision™ + Dual Link System-HRP | Dako EnVision™ + Dual Link System-HRP | Dako EnVision™ + Dual Link System-HRP |
| Linker molecule | None | None | Mouse anti-HRP 5 μg/mL | Rabbit anti-HRP 5 μg/mL |
| Second binding agent | None | Dako EnVision™ + Dual Link System-HRP | Dako EnVision™ + Dual Link System-HRP | Dako EnVision™ + Dual Link System-HRP |
| p53 Gastric Cancer | | | | |
| CDX-2 Colorectal Cancer | | | | |

FIG. 5

| | Comparative Example 10 | Example 8 | Comparative Example 11 | Example 9 |
|---|---|---|---|---|
| Biological sample | p53 Gastric Cancer | p53 Gastric Cancer | CDX-2 Colorectal Cancer | CDX-2 Colorectal Cancer |
| First binding agent | Anti-Mouse Poly-HRP ×1/10 | Anti-Mouse Poly-HRP ×1/10 | Anti-Rabbit Poly-HRP ×1/10 | Anti-Rabbit Poly-HRP ×1/10 |
| Linker molecule | None | Mouse anti-HRP 5 μg/mL | None | Rabbit anti-HRP 5 μg/mL |
| Second binding agent | Anti-Mouse Poly-HRP ×1/10 | Anti-Mouse Poly-HRP ×1/10 | Anti-Rabbit Poly-HRP ×1/10 | Anti-Rabbit Poly-HRP ×1/10 |
| Micrograph | | | | |

FIG. 6

| | Comparative Example 12 | Comparative Example 13 | Example 10 | Example 11 | Example 12 | Comparative Example 14 |
|---|---|---|---|---|---|---|
| First binding agent | ImmPRESS UNIVERSAL | ImmPRESS UNIVERSAL | ImmPRESS UNIVERSAL | ImmPRESS UNIVERSAL | ImmPRESS UNIVERSAL | ImmPRESS UNIVERSAL |
| Linker molecule | None | None | Mouse anti-HRP 5 μg/mL | Rabbit anti-HRP 5 μg/mL | Goat anti-HRP 5 μg/mL | None |
| Second binding agent | None | ImmPRESS UNIVERSAL | ImmPRESS UNIVERSAL | ImmPRESS UNIVERSAL | ImmPRESS Anti-Goat Ig | ImmPRESS Anti-Goat Ig |
| p53 Gastric Cancer | | | | | | |
| CDX-2 Colorectal Cancer | | | | | | |

FIG. 7

|  | Comparative Example 15 | Comparative Example 16 | Example 13 | Comparative Example 17 | Comparative Example 18 | Example 14 |
|---|---|---|---|---|---|---|
| First binding agent | 5 μg/mL PLL M W 2700 | 5 μg/mL PLL M W 2700 | 5 μg/mL PLL M W 2700 | 5 μg/mL PLL M W 7500 | 5 μg/mL PLL M W 7500 | 5 μg/mL PLL M W 7500 |
| Linker molecule | None | None | Mouse anti-HRP 5 μg/mL | None | None | Mouse anti-HRP 5 μg/mL |
| Second binding agent | None | 7.5 μg/mL PLL M W 2700 | 7.5 μg/mL PLL M W 2700 | None | 7.5 μg/mL PLL M W 7500 | 7.5 μg/mL PLL M W 7500 |
| p53 Gastric Cancer |  |  |  |  |  |  |

|  | Comparative Example 19 | Comparative Example 20 | Example 15 | Comparative Example 21 | Comparative Example 22 | Example 16 |
|---|---|---|---|---|---|---|
| First binding agent | 5 μg/mL PLL M W 9200 | 5 μg/mL PLL M W 9200 | 5 μg/mL PLL M W 9200 | 5 μg/mL POD polymer No PLL | 5 μg/mL POD polymer No PLL | 5 μg/mL POD polymer No PLL |
| Linker molecule | None | None | Mouse anti-HRP 5 μg/mL | None | None | Mouse anti-HRP 5 μg/mL |
| Second binding agent | None | 7.5 μg/mL PLL M W 9200 | 7.5 μg/mL PLL M W 9200 | None | 7.5 μg/mL POD polymer No PLL | 7.5 μg/mL POD polymer No PLL |
| p53 Gastric Cancer |  |  |  |  |  |  |

FIG. 8

| | Comparative Example 23 | Comparative Example 24 | Example 17 |
|---|---|---|---|
| First binding agent | AP-M 10 μg/mL 10min. | AP-M 10 μg/mL 10min. | AP-M 10 μg/mL 10min. |
| Linker molecule | None | None | Mouse anti-AP 5 μg/mL 10min. |
| Second binding agent | None | AP-M 10 μg/mL 10min. | AP-M 10 μg/mL 10min. |
| p53 Gastric Cancer | | | |

| | Comparative Example 25 | Comparative Example 26 | Example 18 |
|---|---|---|---|
| First binding agent | AP-R 10 μg/mL 10min. | AP-R 10 μg/mL 10min. | AP-R 10 μg/mL 10min. |
| Linker molecule | None | None | Rabbit anti-AP 5 μg/mL 10min. |
| Second binding agent | None | AP-R 10 μg/mL 10min. | AP-R 10 μg/mL 10min. |
| CDX-2 Colorectal cancer | | | |

|  | Example 20 | Example 21 | Example 22 | Example 23 | Example 24 |
|---|---|---|---|---|---|
| First binding agent | (M)5+(R)5, 10min. | (M)5+(R)5+PEG, 10min. | (M)5+(R)5, 10min. | (M)5+(R)5, 10min. | (M)5+(R)5+PEG, 10min. |
| Linker molecule | (HP-O3)2.5+(2H11)2.5, 10min. | (HP-O3)2.5+(2H11)2.5, 10min. | (HP-O3)2.5+(2H11)2.5+PEG, 10min. | (HP-O3)2.5+(2H11)2.5+PEG, 10min. | (HP-O3)2.5+(2H11)2.5+PEG, 10min. |
| Second binding agent | (M)5, 10min. | (M)5, 10min. | (M)5+PEG, 10min. | (M)5, 10min. | (M)5+PEG, 10min. |
| CDX-2 Colorectal cancer | | | | | |

FIG. 11

COMBINATION PRODUCT FOR DETECTING TARGET MARKER

CROSS-REFERENCE TO RELATED APPLICATIONS

The present patent application claims priority based on Japanese Patent Application No. 2014-89675 filed on Apr. 23, 2014, the entire disclosure of which is incorporated herein by reference.

TECHNICAL FIELD

The present invention relates to a combination product for detecting a target marker and a detection method using the same.

BACKGROUND ART

By virtue of recent advancement of immunochemistry, immunoassays which ensure sensitive detection of a trace amount of a substance by use of an antigen-antibody reaction are widely used. A common immunoassay is, for example, immunostaining methods.

Immunostaining methods are intended to detect a specific substance on a cell or a tissue section using, for example, an antibody which recognizes the substance. Among these methods, those using an enzyme as a detectable substance are referred to as immunoenzyme techniques. Methods which have been developed as the immunoenzyme techniques include direct methods using a primary antibody labeled with an enzyme capable of visualizing the antigen and indirect methods comprising labeling a secondary antibody without labeling a primary antibody.

Further, in recent years, further high sensitivity is required in order to visualize a small amount of an antigen protein distributed in tissues and cells or to verify an antigen substance whose antigenicity is significantly impaired by formalin fixation or paraffin embedding treatment, and various amplification methods, which are modified immunoenzyme techniques, have been developed one after another. Examples of those amplification methods include, in ascending order of sensitivity, direct method<indirect method<PAP (peroxidase anti-peroxidase) method<ABC (avidin-biotin-peroxidase complex) method<LSAB (labeled streptavidin biotin) method<polymer method<CSA (catalyzed signal amplification) method. (Non-Patent Document 1)

Among the above amplification methods, the most popular, highly-sensitive and simple methods are, at present, polymer methods.

One conventional polymer method is, for example, a method comprising reacting a primary antibody with a target marker such as an antigen, and then reacting a polymer reagent (in which many enzymes and secondary antibodies are bound to a polymer) with the reaction product, thereby forming a complex of the antigen, primary antibody, secondary antibody, polymer and enzyme. Color development of a substrate through the use of the enzyme activity in this complex allows visualization of the target marker (Non-Patent Document 1).

Also, another polymer method is, for example, a method comprising reacting a bridge reagent (which is also named variously by makers, e.g., linker, probe or post-primary) between the primary antibody and the polymer reagent in the above conventional polymer method for signal amplification. It is said that, as a result, this method can be expected to have twice to five times as high sensitivity as that of the above method (Non-Patent Document 1).

In recent years, there has been further developed a new polymer method comprising reacting an additional polymer reagent (second polymer reagent) with the above polymer reagent (first polymer reagent) for signal amplification (Patent Document 1).

However, even when the conventional polymer method is employed, staining at a desired level cannot be attained, in some cases, because of an extremely small amount of the target marker, decreased antigenicity, and so forth. In such a technical situation, a means for detecting a target marker simply and with higher sensitivity is still demanded.

PRIOR ART DOCUMENTS

Non-Patent Document

Non-Patent Document 1: Shingo Kamoshida, Immunostaining technique from basics—How to surely stain-, Histochemistry and Cytochemistry 2012, edited by Japan Society of Histochemistry and Cytochemistry, 2012, p. 11-25

Patent Document

Patent Document 1: JP 2007-513334 T

SUMMARY OF INVENTION

An object of the present invention is to detect a target marker expressed in a biological sample simply and with high sensitivity.

The present inventors have now found that, when a plurality of binding agents labeled with labeling substances and a specific linker molecule are combined to detect a target marker, the target marker can be detected simply and with remarkably high sensitivity. The present invention is based on such finding.

The present invention includes the following inventions.

[1] A combination product for detecting a target marker in a biological sample in combination with a target marker binding molecule which is capable of binding specifically to the target marker, the combination product comprising, at least:

(a) a first binding agent comprising a first binding molecule which is capable of directly or indirectly binding specifically to the target marker binding molecule, and a labeling substance;

(b) a linker molecule which is capable of binding specifically to the first binding agent, and (c) a second binding agent which is capable of binding specifically to the linker molecule, and comprises a second binding molecule and a labeling substance.

[2] The combination product according to item [1], wherein the linker molecule is capable of binding specifically to the labeling substance.

[3] The combination product according to item [1] or [2], wherein the linker molecule is an antibody or an antigen binding fragment thereof.

[4] The combination product according to any one of items [1] to [3], wherein the labeling substance is at least one selected from a chemiluminescent label, a metal particle, a fluorescent label, an enzyme label, a coenzyme label, a labeled antibody, a dye, a bioluminescent label, a hapten and a polymer particle.

[5] The combination product according to any one of items [1] to [4], wherein the first binding agent is a structure in which the first binding molecule and the labeling substance are connected with each other directly or indirectly via a carrier.

[6] The combination product according to any one of items [1] to [5], wherein the second binding agent is a structure in which the second binding molecule and the labeling substance are connected with each other directly or indirectly via a carrier.

[7] The combination product according to any one of items [1] to [6], wherein the first binding molecule is an antibody or an antigen binding fragment thereof.

[8] The combination product according to any one of items [1] to [7], wherein the second binding molecule is an antibody or an antigen binding fragment thereof.

[9] The combination product according to any one of items [1] to [8], which is further combined with the target marker binding molecule.

[10] The combination product according to any one of items [1] to [9], which is in the form of a kit.

[11] A method for detecting a target marker in a biological sample obtained from a subject, comprising the steps of:
(i) contacting a target marker binding molecule preliminarily bound specifically to the target marker with a first binding agent, thereby obtaining a first complex;
(ii) contacting the first complex with a linker molecule, thereby obtaining a second complex; and
(iii) contacting the second complex with a second binding agent, thereby obtaining a third complex,
wherein the first binding agent comprises a first binding molecule which is capable of directly or indirectly binding specifically to the target marker binding molecule, and a labeling substance;
wherein the linker molecule is capable of binding specifically to the first binding agent; and
wherein the second binding agent is capable of binding specifically to the linker molecule and comprises a second binding molecule and a labeling substance.

[12] The method according to item [11], further comprising the step of detecting the labeling substance in the third complex.

[13] The method according to item [11] or [12], wherein the linker molecule is an antibody or an antigen binding fragment thereof.

[14] The method according to any one of items [11] to [13], wherein the linker molecule is capable of binding specifically to the labeling substance.

[15] The method according to any one of items [11] to [14], wherein the labeling substance is at least one labeling substance selected from a chemiluminescent label, a metal particle, a fluorescent label, an enzyme label, a coenzyme label, a labeled antibody, a dye, a bioluminescent label, a hapten and a polymer particle.

[16] The method according to any one of items [11] to [15], wherein the first binding agent is a structure in which the first binding molecule and the labeling substance are connected with each other directly or indirectly via a carrier.

[17] The method according to any one of items [11] to [16], wherein the second binding agent is a structure in which the second binding molecule and the labeling substance are connected with each other directly or indirectly via a carrier.

[18] The method according to any one of items [11] to [17], wherein the first binding molecule is an antibody or an antigen binding fragment thereof.

[19] The method according to any one of items [11] to [18], wherein the second binding molecule is an antibody or an antigen binding fragment thereof.

[20] Use of a combination product for detecting a target marker in a biological sample in combination with a target marker binding molecule which is capable of binding specifically to the target marker, the combination product comprising, at least:
(a) a first binding agent comprising a first binding molecule which is capable of directly or indirectly binding specifically to the target marker binding molecule, and a labeling substance;
(b) a linker molecule which is capable of binding specifically to the first binding agent; and
(c) a second binding agent which is capable of binding specifically to the linker molecule, and comprises a second binding molecule and a labeling substance,
wherein the linker molecule is capable of binding specifically to the labeling substance.

According to the present invention, the target marker can be detected simply and with remarkably high sensitivity.

BRIEF DESCRIPTION OF THE DRAWINGS

FIG. 2 shows micrographs which present the results of immunohistochemical staining in Test Example 1 (Comparative Examples 1 and 2).

FIG. 3 shows micrographs which present the results of immunohistochemical staining in Test Example 2 (Examples 1 and 2 and Comparative Examples 3 and 4).

FIG. 4 shows micrographs which present the results of immunohistochemical staining in Test Example 3 (Examples 3 to 5 and Comparative Examples 5 to 7).

FIG. 5 shows micrographs which present the results of immunohistochemical staining in Test Example 4:4-1 (Examples 6 and 7 and Comparative Examples 8 and 9).

FIG. 6 shows micrographs which present the results of immunohistochemical staining in Test Example 4:4-2 (Examples 8 and 9 and Comparative Examples 10 and 11).

FIG. 7 shows micrographs which present the results of immunohistochemical staining in Test Example 4:4-3 (Examples 10 to 12 and Comparative Examples 12 to 14).

FIG. 8 shows micrographs which present the results of immunohistochemical staining in Test Example 5 (Examples 13 to 16 and Comparative Examples 15 to 22).

FIG. 9 shows micrographs which present the results of immunohistochemical staining in Test Example 6:6-1 (Example 17 and Comparative Examples 23 and 24).

FIG. 10 shows micrographs which present the results of immunohistochemical staining in Test Example 6:6-2 (Example 18 and Comparative Examples 25 and 26).

FIG. 11 shows micrographs which present the results of immunohistochemical staining in Test Example 7: Example 20 carried out in the absence of polyethylene glycol and Examples 21 to 24 carried out in the presence of polyethylene glycol.

DETAILED DESCRIPTION OF THE INVENTION

Combination Product

Figure 1:
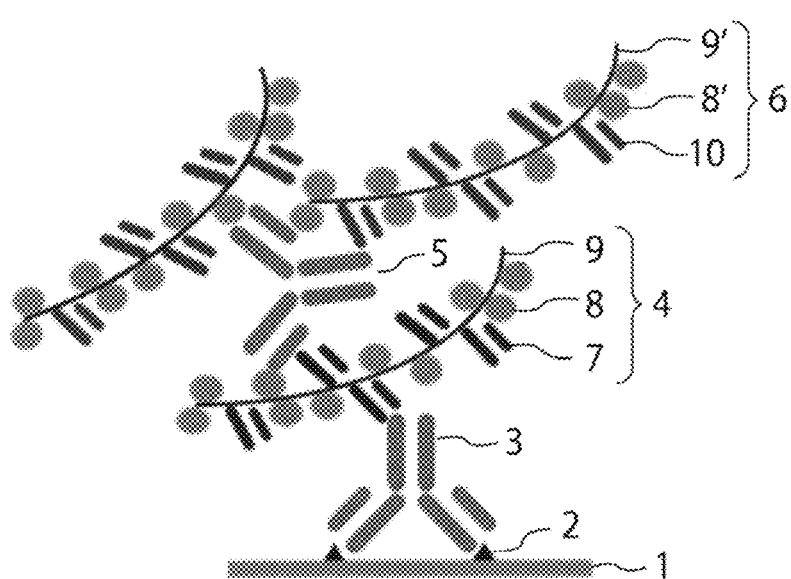
FIG. 1 is a schematic diagram concerning a method for detecting a target marker according to the present invention.

The combination product of the present invention is the one for detecting a target marker in a biological sample in combination with a target marker binding molecule which Is capable of binding specifically to the target marker, characterized by comprising, at least:

(a) a first binding agent comprising a first binding molecule which Is capable of directly or indirectly binding specifically to the target marker binding molecule, and a labeling substance;

(b) a linker molecule which Is capable of binding specifically to the first binding agent; and (c) a second binding agent which Is capable of binding specifically to the linker molecule, and comprises a second binding molecule and a labeling substance.

Hereinafter, one embodiment of a detection method using the combination product of the present invention will be explained in accordance with FIG. 1, though not particularly limiting the present invention.

In FIG. 1, a target marker 2 to be detected is expressed on a biological sample 1. In order to trap this target marker 2, a target marker binding molecule 3 is preliminarily bound specifically to the target marker 2.

Then, a first binding agent 4, a linker molecule 5 and a second binding agent 6 are provided as reagents for detecting the target marker 2.

Here, the first binding agent 4 is composed of a first binding molecule 7 which is capable of directly or indirectly binding specifically to the target marker binding molecule 3, a labeling substance 8 and a carrier 9 (such as a polymer).

Also, the second binding agent 6 is a structure which is capable of binding specifically to the linker molecule 5. In FIG. 1, the second binding agent 6 is composed of a second binding molecule 10 which is capable of binding specifically to the linker molecule 5, a labeling substance 8' and a carrier 9' (such as a polymer).

Also, the linker molecule 5 comprises at least three binding sites which are capable of binding specifically to the labeling substance 8, the second binding molecule 10 and the labeling substance 8'.

In FIG. 1, the combination of the preliminarily-provided detection reagents as described above can be used to detect the target marker through the following first to third steps.

In the first step, the target marker binding molecule 3 bound to the target marker 2 is contacted with the first binding agent 4, thereby obtaining a first complex (1 to 4).

Then, in the second step, the first complex (1 to 4) is contacted with the linker molecule 5, thereby obtaining a second complex (1 to 5).

Thereafter, in the third step, the second complex (1 to 5) is contacted with the second binding agent 6, thereby obtaining a third complex (1 to 6). Here, the linker molecule 5 and the second binding agent 6 are stably bound to each other via at least two binding sites, i.e., the second binding molecule 10 and the labeling substance 8'.

Through the above first to third steps, the target marker 2 can be labeled both by the labeling substance 8 and by the labeling substance 8' and detected with high detection sensitivity.

Biological Sample

The biological sample of the present invention refers to a sample obtained from any of subjects, e.g., an animal (preferably a mammal, more preferably a human), a plant or a bacterium. The above biological sample may be composed either of a eukaryotic or prokaryotic cell or of a tissue or cell.

Target Marker

The target marker in the biological sample of the present invention refers to any molecule present in the biological sample. Examples of the above target marker include proteins and protein fragments thereof, peptides, nucleic acids, lipids, glycolipids, sugars, polysaccharides and starch. Here, the protein includes modified proteins such as glycoproteins, lipoproteins, phosphoproteins and methylated proteins, and the nucleic acid includes DNA and RNA. Also, the above target marker may be either expressed on the surface of the biological sample, e.g., membrane bound, or contained in the interior of the biological sample, e.g., within the cell membrane, cytoplasm or nucleus.

Target Marker Binding Molecule

The target marker binding molecule of the present invention is not particularly limited so long as it is capable of binding specifically to the target marker in the biological sample, and examples thereof include antibodies or fragments thereof (including an antigen-binding fragment), DNA, RNA, nucleic acid probes such as a peptide nucleic acid (PNA), ligands or receptors.

First Binding Agent

The first binding agent of the present invention comprises a first binding molecule which is capable of directly or indirectly binding specifically to a target marker binding molecule, and a labeling substance. The first binding molecule and the labeling substance according to the present invention may be directly bound to each other at any site so long as the effect of the present invention would not be inhibited. Also, the first binding agent may comprise a carrier together with the first binding molecule and the labeling substance according to the present invention. Also, the first binding agent of the present invention may include a hapten label.

First Binding Molecule

The first binding molecule is not limited so long as it is capable of directly or indirectly binding specifically to the target marker binding molecule, but is preferably an antibody, an antigen-binding fragment thereof. Here, the antibody may be of any isotype, i.e., IgG, IgM, IgA, IgD or IgE. Also, examples of the antibody fragment include antigen-binding fragments, preferably Fab, Fab', (Fab')$_2$, Fv, scFv, diabodies, triabodies, tetrabodies or single domain antibodies.

Also, the sentence that the first binding molecule specifically binds "indirectly" to the target marker binding molecule means that a molecule such as a bridge reagent is interposed between the target marker binding molecule and the first binding molecule so that the first binding molecule is capable of binding specifically to the molecule such as a bridge reagent. The bridge reagent is not particularly limited so long as the effect of the present invention would not be inhibited, and examples thereof include antibodies and antigen-binding fragments such as Fab, Fab', (Fab')$_2$, Fv or scFv. The above bridge reagent may further include a hapten label or a fluorescent label.

Labeling Substance in First Binding Agent

The labeling substance in the first binding agent of the present invention is not particularly limited so long as the effect of the present invention would not be inhibited, and examples thereof include chemiluminescent labels, metal particles, fluorescent labels, enzyme labels, coenzyme labels, labeled antibodies, dyes, bioluminescent labels, haptens and polymer particles. Also, the above labeling substance is more preferably labeled with an enzyme usable in an immunoenzyme technique, and examples of such enzymes include horseradish peroxidase (HRP), alkaline phosphatase (AP), β-galactosidase (GAL), glucose-6-phosphate dehydrogenase, β-N-acetylglucosaminidase, β-glucuronidase, invertase, xanthine oxidase, firefly luciferase, and glucose oxidase (GO).

Also, when an enzyme is used as the labeling substance, the substrate thereof is not limited so long as it is a substance which is reacted with the above labeling substance to develop a color. Examples of commonly used substrates for horse radish peroxidase Include 3, 3'-diaminobenzidine (DAB), diaminobenzidine with nickel enhancement, 3-amino-9-ethylcarbazole (AEC), benzidine dihydrochloride (BDHC), Hanker-Yates reagent (HYR), indophane blue (IB), tetramethylbenzidine (TMB), 4-chloro-1-naphtol (CN), α-naphtol pyronin (α-NP), o-dianisidine (OD), 5-bromo-4-chloro-3-indolylphosphate (BCIP), nitro blue tetrazolium (NBT), 2-(p-iodophenyl)-3-p-nitrophenyl-5-phenyl tetrazolium chloride (INT), tetranitro blue tetrazolium (TNBT), and 5-bromo-4-chloro-3-indolyl-β-D-galactoside/ferro-ferricyanide (BCIG/FF).

Also, examples of commonly used substrates for alkaline phosphatase include naphthol-AS-B1-phosphate/fast red TR (NABP/FR), naphthol-AS-MX-phosphate/fast red TR (NAMP/FR), naphthol-AS-B1-phosphate/fast red TR (NABP/FR), naphthol-AS-MX-phosphate/fast red TR (NAMP/FR), naphthol-AS-B1-phosphate/new fuchsin (NABP/NF), bromochloroindolyl phosphate/nitro blue tetrazolium (BCIP/NBT), and 5-bromo-4-chloro-3-indolyl-b-d-galactopyranoside (BCIG).

Carrier in First Binding Agent

Also, the carrier in the first binding agent is not particularly limited so long as the effect of the present invention would not be inhibited, but is preferably a naturally-occurring or synthetic polymer. Also, the molecular weight of the polymer according to the present invention is not particularly limited so long as the effect of the present invention would not be inhibited, but, as one preferred example thereof, the average molecular weight (Mw) can be defined within the range of from 2,000 to 500,000. Such an average molecular weight can be determined, for example, using a standard product of the polymer as an index, by gel filtration (GPC). The above molecular weight range, however, is a mere guide, and molecular weights which are either higher or lower than the above range can be used so long as the object of the present invention would be attained. Suitable examples of such a polymer include polyamino acids, proteins, polynucleotides, polysaccharides or organic synthetic polymers. Also, in order to increase immunoassay sensitivity, many labeling substances are desirably bound to the carrier of the present invention.

For example, a peptide comprising at least two multiple amino groups with binding property may be used as the polyamino acid of the present invention. Examples of the polyamino acid include polyamino acid comprising lysine, arginine, ornithine, glutamine or any other basic amino acid which have an α-amino group, an ε-amino group or any other amino group. Further, specific examples of the polyamino acid include, in addition to polylysines which are polymers of lysine having an ε-amino group, various polyamino acids having lysine and, additionally, other amino acids. Examples of the latter peptide polymer include random copolymers of lysine and glycine, random copolymers of lysine and serine, and random copolymers of lysine and glutamic acid, and those having various molecular weights are commercialized.

Also, examples of the protein according to the present invention include albumins, immunoglobulins or virus-like proteins (VLP).

Examples of the polynucleotide according to the present invention include those comprising one or more constituent unit(s) selected from DNA, PNA, LNA, etc. Also, the polynucleotide of the present invention may be in the form of a dendrimer construct.

Also, examples of the polysaccharide according to the present invention include dextran, agarose, dextrin and soluble starch. Also, a polysaccharide into which an aldehyde group, an amino group or any other active group is introduced can be used as such a polysaccharide. The polysaccharide having an aldehyde group can be easily prepared by reacting sodium periodate with a polysaccharide. An amino group can also be introduced into a polysaccharide by a known method. For example, dextran having an amino group can be prepared by treating dextran with sodium periodate to produce aldehyde groups, then reacting them with diamine, and reducing the reaction products with sodium borohydrate. Also, the introduction of an active group into a polysaccharide can also be performed by a known method. For example, dextran having vinyl groups is obtained by reacting divinyl sulfone with dextran. Examples of the above polysaccharide Include polysaccharide including dextran, carboxymethyl dextran, dextran polyaldehyde, carboxymethyl dextran lactone and cyclodextrin; pullulan, schizophyllan, scleroglucan, xanthan, gellan, O-ethylamine guaran, chitin and chitosan such as 6-O-carboxymethyl chitin and N-carboxymethyl chitosan; derivatized celluloses such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenan, alginate and agarose; synthetic polysaccharides such as ficoll and carboxymethylated ficoll.

Also, examples of the organic synthetic polymer according to the present invention include, preferably, polymers composed of at least one constituent unit selected from the group consisting of (meth)acrylic acid, (meth)acrylamide, (meth)acrylic ester, methyl methacrylate, maleic acid, maleic anhydride, vinyl acetate, vinyl alcohol, vinyl chloroacetate, ethylene glycol, propylene glycol, glycerin, diisocyanate, styrene, isoprene, allylamine and ethyleneimine. More specifically, examples of the organic synthetic polymer include vinyl polymers including poly(acrylic acid), poly(acrylamide), poly(acrylic ester), poly(2-hydroxyethyl methacrylate), poly(methyl methacrylate), poly(maleic acid), poly(maleic anhydride), poly(ethyl-co-vinyl acetate), poly(methacrylic acid), poly(vinyl alcohol), poly(vinyl alcohol-co-vinyl chloroacetate), aminated poly(vinyl alcohol) and co-block polymers thereof; polyethylene glycol (PEG) or polypropylene glycol or poly(ethylene oxide-co-propylene oxide) containing polymer backbones including linear, comb-shaped or branched dendrimers; poly(ethyleneimines); and poly(allylamines).

Second Binding Agent

The second binding agent of the present invention is capable of binding specifically to the linker molecule, and comprises a second binding molecule and a labeling substance. The second binding molecule and the labeling substance according to the present invention may be directly bound to each other at any site so long as the effect of the present invention would not be inhibited. Also, the second binding agent may comprise a carrier together with the second binding molecule and the labeling substance according to the present invention. Also, the second binding agent of the present invention may comprise a hapten label.

Second Binding Molecule

The second binding molecule is not limited so long as it is capable of binding specifically to the linker molecule, but is preferably an antibody, a fragment thereof. Here, the antibody may be of any isotype, i.e., IgG, IgM, IgA, IgD or IgE. Also, examples of the antibody fragment include an antigen-binding fragment, preferably Fab, Fab', (Fab')$_2$, Fv, scFv, diabodies, triabodies, tetrabodies or single domain antibodies.

Labeling Substance in Second Binding Agent

The labeling substance in the second binding agent of the present invention is not particularly limited so long as it does not inhibit the detection of a target marker, but, for example, can be selected from the labeling substances exemplified for the first binding agent. Thus, the labeling substance in the second binding agent may be either the same as or different from that in the first binding agent, but is preferably the same labeling substance. The same labeling substance is especially advantageous in detecting a target marker simply and with high-level detection sensitivity.

Carrier in Second Binding Agent

The carrier in the second binding agent is not particularly limited so long as the effect of the present invention would not be inhibited, but, for example, can be selected from the carriers exemplified for the first binding agent. Thus, the carrier in the second binding agent may be either the same as or different from that in the first binding agent.

Linker Molecule

The linker molecule of the present invention is capable of binding specifically to the first binding agent, as described above. Also, it is preferred that the linker of the present invention is capable of binding specifically both to the first binding agent and to the second binding agent, in view of effective detection of a target marker. Thus, according to one embodiment of the present invention, the linker molecule is capable of binding specifically both to the first binding agent and to the second binding agent. The linker molecule of the present invention may bind specifically to any sites of the first binding agent and the second binding agent so long as the effect of the present invention would not be inhibited, but, preferably, is capable of binding specifically to the labeling substance in the first binding agent and/or the labeling substance in the second binding agent, and, more preferably, is capable of binding specifically both to the labeling substance in the first binding agent and to the labeling substance in the second binding agent.

Also, the site at which the linker molecule of the present invention is specifically bound by the second binding molecule in the second binding agent may be different from that for the labeling substance as shown in FIG. 1. Thus, according to one embodiment of the present invention, the linker molecule includes at least two binding sites at which it is capable of binding specifically to the second binding agent.

Examples of the above linker molecule include an antibody or a fragment thereof. Here, the antibody may be of any isotype, i.e., IgG, IgM, IgA, IgD or IgE. Also, the antibody fragment includes an antigen-binding fragment such as Fab, Fab', (Fab')$_2$, Fv or scFv. The above linker molecule may further include a hapten label different from the immunogen used in the production of the linker molecule or a fluorescent substance label. Also, according to one embodiment of the present invention, a plurality of antibodies or their antigen-binding fragments which are connected via a carrier such as a polymer are excluded from the above linker molecule.

Polyethylene Glycol

In the present invention, at least one reagent of the first binding agent, linker molecule and second binding agent is preferably subjected to an immunoreaction in the coexistence of polyethylene glycol in the detection of the target marker. The order of mixing the above reagent with polyethylene glycol for coexistence is not particularly limited in the present invention. For example, it is possible either to start an immunoreaction using the above reagent and rapidly add polyethylene glycol in turn, or to preliminarily mix the above reagent with polyethylene glycol and then carry out an immunoreaction. The above reagent and polyethylene glycol are preferably allowed to coexist simultaneously with or before the initiation of an immunoreaction, from the viewpoint of effective enhancement of the immunoreaction according to the present invention.

The molecular weight of polyethylene glycol used in the present invention is not particularly limited so long as the effect of the present invention is obtained, but, as one suitable example, the average molecular weight (MW) can be defined within the range of from 2,000 to 20,000. Such an average molecular weight can be determined, for example, using a standard product of polyethylene glycol as an index by gel filtration (GPC).

Combination Product

The combination product of the present invention comprises, in combination, the above (a) first binding agent, (b) linker molecule and (c) second binding agent, in order to detect a target marker in a biological sample in combination with a target marker binding molecule which is capable of binding specifically to the target marker. The embodiment of the combination product according to the present invention is not particularly limited so long as the effect of the present invention would not be inhibited. For example, the (a) first binding agent, (b) linker molecule and (c) second binding agent may be either integrally constituted like a composition, or constituted as separate bodies like a detection kit or a detection system. Thus, the combination product of the present invention is preferably provided in the form of a composition or a kit. Also, the combination product of the present invention may comprise reagents other than (a) to (c), so long as the effect of the present invention would not be inhibited.

Also, according to one embodiment of the present invention, the combination product of the present invention further comprises, in combination, the above target marker binding molecule, in addition to the above (a) to (c).

Method for Detecting Target Marker in Biological Sample

According to the present invention, as described above, the (a) first binding agent, (b) linker molecule and (c) second binding agent and a target marker binding molecule are used together, thereby making it possible to detect the target marker in a biological sample obtained from a subject simply and with high-level detection sensitivity. Thus, according to one embodiment of the present invention, there is provided a method for detecting a target marker in a biological sample obtained from a subject, comprising the steps of:

(i) contacting a target marker binding molecule preliminarily bound specifically to the target marker with a first binding agent, thereby obtaining a first complex;

(ii) contacting the first complex with a linker molecule, thereby obtaining a second complex; and (iii) contacting the second complex with a second binding agent, thereby obtaining a third complex, wherein the above first binding agent comprises a first binding molecule which is capable of directly or indirectly binding specifically to the above target marker binding molecule, and a labeling substance;

wherein the above bindable linker molecule is capable of binding specifically to the first binding agent; and wherein the second binding agent is capable of binding specifically to the linker molecule and comprises a second binding molecule and a labeling substance.

In the above respective contacting steps (i) to (iii), the first complex, second complex and third complex can be obtained by using a known method such as mixing the respective ingredients.

In the above respective contacting steps (i) to (iii), the first binding agent, linker molecule and second binding agent can preferably be added as a solution.

The concentration of the first binding agent in the above solution in step (i) is not particularly limited, but can be defined within the range of from 1 to 15 µg/mL.

The concentration of the linker molecule in the above solution in step (ii) is not particularly limited, but can be defined within the range of from 0.5 to 15 µg/mL.

The concentration of the second binding agent in the above solution in step (iii) is not particularly limited, but can be defined within the range of from 1 to 15 µg/mL.

Also, at least one or all of the respective contacting steps (i) to (iii) is/are preferably carried out in the coexistence of polyethylene glycol, in view of enhancement of the detection sensitivity for the target marker. The concentration of polyethylene glycol in the above solutions used in steps (i) to (iii) is not particularly limited, but can be defined within the range of from 0.5 to 20 wt %.

Also, the method of the present invention may further comprise the step of detecting the labeling substance in the first binding agent and the labeling substance in the second binding agent.

The method for detecting the labeling substance in the first binding agent and the labeling substance in the second binding agent according to the present invention may appropriately be set by those skilled in the art according to the kinds and properties of the labeling substances. For example, various known detection methods, including immunostaining, in situ hybridization, flow cytometry, enzyme immunoassay (EIA), enzyme-linked immunosorbent assay (ELISA) and Western blot, can be used. Preferably, the detection method is immunohistochemical staining or in situ hybridization such as chromogenic in situ hybridization (CISH).

Details of the reaction conditions for the respective contacting steps (i) to (iii) and the detection of the labeling substances, according to the present invention, can be determined by those skilled in the art in accordance with a known technique.

EXAMPLES

Hereinafter, the present invention is described in more detail by way of Examples, but is not limited to these Examples. Details of the units and measurement conditions used in the present invention are in conformity with the provision of JIS (Japanese Industrial Standards), unless otherwise specified.

Test Example 1: Study of High-Sensitivity Staining Method Using First Binding Agent Alone and High-Sensitivity Staining Method Using First Binding Agent and Second Binding Agent Alone In this Test Example, a reaction system using the first binding agent alone (Comparative Example 1) and a reaction system using the first binding agent and the second binding agent alone (Comparative Example 2) were compared in terms of detection sensitivity for the target marker.

Reagent Preparation

1. Preparation of First Binding Agent

The first binding agent (polymer reagent) was produced in accordance with the descriptions in paragraphs [0031] to [0040] of JP 2001-181299 A.

Specifically, a polymer reagent (M) comprising peroxidases and Fab' fragments of anti-mouse Ig (animal species: goat) bound to an amino acid polymer and a polymer reagent (R) comprising peroxidases and Fab' fragments of anti-rabbit Ig (animal species: goat) bound to an amino acid polymer were mixed in each amount of 5 µg/mL, thereby preparing a cocktail polymer reagent (MULTI).

2. Preparation of Second Binding Agent

A polymer reagent (G) comprising peroxidases and Fab' fragments of anti-goat Ig (animal species: rabbit) bound to an amino acid polymer was prepared in 7.5 µg/mL.

Immunohistochemical Staining

1. Deparaffinization, Peroxidase Blocking and Antigen Retrieval Treatment

A. Provision of Specimen Slide

A tissue section was sliced into 3 µm and mounted onto a MAS-coated slide glass. Thereafter, the slide glass was dried overnight in an incubator at 37° C.

B. Deparaffinization (I) Xylene Treatment (3 Minutes×3 Times)

The slide was immersed in xylene for 3 minutes. Thereafter, an excess liquid was shaken off, and then the slide was immersed in another xylene for 3 minutes. Thereafter, an excess liquid was shaken off, and the slide was immersed in still another xylene for 3 minutes.

(II) Ethanol Treatment (3 Minutes×4 Times)

The slide was immersed in 100% ethanol for 3 minutes. An excess liquid was shaken off, and the slide was immersed in another 100% ethanol for 3 minutes. This operation was carried out twice more.

(III) Washing

Excess ethanol was shaken off, and the slide was washed in PBS (the container was changed twice, respectively for 3 minutes).

C. Treatment by Antigen Retrieval

Antigen Retrieval Solution pH9 (NICHIREI BIOSCIENCES INC.) was used for heating treatment in an autoclave for 20 minutes, and allowed to stand at room temperature for 20 minutes. Thereafter, the slide was washed in PBS for 3 minutes×twice.

D. Peroxidase Blocking

Endogenous peroxidase was blocked. After drained, the slide was immersed in a 3V/V % hydrogen peroxide solution for 10 minutes. Thereafter, the slide was washed in PBS for 3 minutes×twice.

2. Addition•Reaction of First Antibody or Negative Control (First Antibody Diluent)

Onto the slide glass from which an excess liquid was shaken off, a first antibody or a first antibody diluent was added dropwise to cause a reaction in a moist chamber at 25° C. for 30 minutes. Thereafter, the slide glass was washed in PBS for 3 minutes×twice. The combination of tissue and first antibody used in the study is as follows.

Gastric cancer . . . anti-human p53 gene product monoclonal antibody (DO-7) (NICHIREI BIOSCIENCES INC.) used diluted 3-fold.

Colorectal cancer . . . anti-CDX-2 rabbit monoclonal antibody (NICHIREI BIOSCIENCES INC.) used as it was.

3. Reaction with First Binding Agent

Onto the slide glass from which an excess liquid was shaken off, the cocktail polymer reagent (MULTI) was added dropwise to cause a reaction in a moist chamber at 25° C. for 10 minutes. Thereafter, the slide glass was washed in PBS for 3 minutes×twice. Incidentally, this reaction was carried out in both of Comparative Examples 1 and 2.

4. Reaction with Second Binding Agent

Onto the slide glass from which an excess liquid was shaken off, the polymer reagent (G) was added dropwise to cause a reaction in a moist chamber at 25° C. for 10 minutes. Thereafter, the slide glass was washed in PBS for 3 minutes× twice. Incidentally, this reaction was carried out only in Comparative Example 2.

5. Addition•Reaction of Substrate Solution

Onto the slide glass from which an excess liquid was shaken off, N-Histofine® DAB-2V (NICHIREI BIOSCIENCES INC.) was added dropwise to cause a reaction at room temperature for 5 minutes. Thereafter, the slide glass was washed with running water for 5 minutes.

6. Counter Staining, Dehydration•Cleaning, Mounting

A. Counter Staining

After drained, the slide glass was immersed in a Mayer's hematoxylin solution for 30 seconds. Thereafter, the slide glass was washed with running water for 5 minutes.

B. Dehydration•Cleaning

Draining was followed by dehydration with ethanol and cleaning with xylene. Here, ethanol was used for dehydration through passage×three times and still standing for 5 minutes×once. Xylene was used for cleaning through passage×once and still standing for 5 minutes×twice.

C. Mounting

Permanent Mounting Media (Non-Aqueous) (NICHIREI BIOSCIENCES INC.) was used for mounting.

The above staining results were as shown in FIG. 2. Here, the micrographs of the respective stained tissues shown in FIG. 2 were taken using an optical microscope (Olympus Corporation) with an ocular lens (10) and an objective lens (4×).

The reaction system of the first binding agent and the second binding agent alone (Comparative Example 2) provided slightly improved staining sensitivity, as compared with the reaction system of the first binding agent alone (Comparative Example 1). However, no staining sensitivity at a desired level could be obtained.

Incidentally, no background staining occurred in the negative control.

Test Example 2: Study of High-Sensitivity Staining Method Using First Binding Agent, Linker Molecule and Second Binding Agent It was reviewed whether the staining sensitivity could be improved by reaction systems using the first binding agent, the linker molecule and the second binding agent, i.e., reaction systems comprising the linker molecule Interposed between the first binding agent and the second binding agent, as compared with reaction systems using the first binding agent alone or reaction systems using the first binding agent and the second binding agent alone.

In this test, among such reaction systems using the first binding agent, the linker molecule and the second binding agent, a reaction system using the linker molecule (1 μg/mL of an anti-HRP antibody) was defined as Example 1, and a reaction system using the linker molecule (5 μg/mL of an anti-HRP antibody) was defined as Example 2.

Also, a reaction system using the first binding agent alone was defined as Comparative Example 3, and a reaction system using the first binding agent and the second binding agent alone was defined as Comparative Example 4.

Reagent Preparation

1. Preparation of First Binding Agent

A polymer reagent (M) comprising peroxidases and Fab' fragments of anti-mouse Ig (animal species: goat) bound to an amino acid polymer and a polymer reagent (R) comprising peroxidases and Fab' fragments of anti-rabbit Ig (animal species: goat) bound to an amino acid polymer were mixed in each amount of 5 μg/mL, thereby preparing a cocktail polymer reagent (MULTI).

2. Preparation of Linker Molecule

A goat anti-HRP antibody (polyclonal) (Pierce) was prepared in 1 μg/mL or 5 μg/mL.

3. Preparation of Second Binding Agent

A polymer reagent (G) comprising peroxidases and Fab' fragments of anti-goat Ig (animal species: rabbit) bound to an amino acid polymer was prepared in 7.5 μg/mL.

Immunohistochemical Staining

1. Deparaffinization, Peroxidase Blocking and Antigen Retrieval Treatment

These procedures were performed similarly as in Test Example 1.

2. Addition•Reaction of First Antibody or Negative Control (First Antibody Diluent)

These procedures were performed similarly as in Test Example 1.

3. Reaction with First Binding Agent

Onto the slide glass from which an excess liquid was shaken off, the cocktail polymer reagent (MULTI) was added dropwise to cause a reaction in a moist chamber at 25° C. for 10 minutes. Thereafter, the slide glass was washed in PBS for 3 minutes×twice. Incidentally, this reaction was carried out in Examples 1 and 2 and Comparative Examples 3 and 4.

4. Reaction with Linker Molecule

Onto the slide glass from which an excess liquid was shaken off, the goat anti-HRP antibody was added dropwise to cause a reaction in a moist chamber at 25° C. for 10 minutes. Thereafter, the slide glass was washed in PBS for 3 minutes×twice. Incidentally, this reaction was carried out in Examples 1 and 2 alone.

5. Reaction with Second Binding Agent

Onto the slide glass from which an excess liquid was shaken off, the polymer reagent (G) was added dropwise to cause a reaction in a moist chamber at 25° C. for 10 minutes. Thereafter, the slide glass was washed in PBS for 3 minutes× twice. Incidentally, this reaction was carried out in Examples 1 and 2 and Comparative Example 4.

6. Addition•Reaction of Substrate Solution

These procedures were performed similarly as in Test Example 1.

7. Counter Staining, Dehydration•Cleaning, Mounting

These procedures were performed similarly as in Test Example 1.

The results were as shown in FIG. 3. Here, the micrographs of the respective stained tissues shown in FIG. 3 were taken using an optical microscope (Olympus Corporation) with an ocular lens (10×) and an objective lens (4×).

The reaction systems (Examples 1 and 2) comprising the linker molecule (anti-HRP antibody) held between the first binding agent and the second binding agent provided significantly improved staining sensitivity, as compared with the reaction system using the first binding agent alone or the reaction system using the first binding agent and the second binding agent alone.

Incidentally, no background staining occurred in the negative control.

Test Example 3: Study of Type of Antibody Used as Linker Molecule

A test was conducted, by a similar test method as in Test Example 2, using polymer reagents and anti-HRP antibodies as indicated in the following Table 1, while the immunized animal species (mouse, rabbit or goat) for the anti-HRP antibodies was changed.

2. Preparation of Linker Molecule

A mouse anti-HRP antibody (clone: HP-03) (TFS) was prepared in 5 µg/mL.

TABLE 1

| | Comparative Example 5 | Example 3 | Comparative Example 6 | Example 4 | Comparative Example 7 | Example 5 |
|---|---|---|---|---|---|---|
| First binding agent | Polymer reagent (M) 5 µg/mL + polymer reagent (R) 5 µg/mL | | | | | |
| Linker molecule | None | Mouse anti-HRP antibody 5 µg/mL (TFS, clone: HP-03) | None | Rabbit anti-HRP antibody 5 µg/mL (NICHIREI BIOSCIENCES INC., polyclonal) | None | Goat anti-HRP antibody 5 µg/mL (Pierce, polyclonal) |
| Second binding agent | Polymer reagent (M) 7.5 µg/mL | | Polymer reagent (R) 7.5 µg/mL | | Polymer reagent (G) 7.5 µg/mL | |

The results were as shown in FIG. 4. Here, the micrographs of the respective stained tissues shown in FIG. 4 were taken using an optical microscope (Olympus Corporation) with an ocular lens (10×) and an objective lens (4×).

Whichever the immunized animal species—antibody was used as the linker molecule, the reaction systems (Examples 3 to 5) using the first binding agent, the linker molecule and the second binding agent each provided significantly improved staining sensitivity, as compared with the reaction systems (Comparative Examples 5 to 7) using the first binding agent and the second binding agent alone. Incidentally, no background staining occurred in the negative control.

Test Example 4: Study of Types of First Binding Agent and Second Binding Agent 4-1: Use of Conjugate of Whole Antibody and Dextran (Carrier) (First Binding Agent and Second Binding Agent)

A polymer reagent (EnVision Dual Link System-HRP, DAKO) comprising whole IgG antibodies and peroxidases bound to a dextran was used as the first binding agent and the second binding agent, and a comparative test on staining sensitivity was conducted in accordance with the following procedures.

Incidentally, a reaction system using the first binding agent, the linker molecule (mouse anti-HRP antibody) and the second binding agent was defined as Example 6; a reaction system using the first binding agent, the linker molecule (rabbit anti-HRP antibody) and the second binding agent was defined as Example 7; a reaction system using the first binding agent alone was defined as Comparative Example 8; and a reaction system using the first binding agent and the second binding agent alone was defined as Comparative Example 9.

Reagent Preparation

1. Preparation of First Binding Agent

A polymer reagent comprising whole IgG antibodies and peroxidases bound to a dextran (EnVision Dual Link System-HRP, DAKO) was used as it was. Specifically, the polymer reagent is a mixture of a polymer reagent (M) comprising peroxidases and anti-mouse IgG antibodies (animal species: goat) bound to a dextran polymer and a polymer reagent (R) comprising peroxidases and anti-rabbit IgG antibodies (animal species: goat) bound to a dextran polymer.

A rabbit anti-HRP antibody (polyclonal) (NICHIREI BIOSCIENCES INC.) was prepared in 5 µg/mL.

3. Preparation of Second Binding Agent

The polymer reagent comprising whole IgG antibodies and peroxidases bound to a dextran (EnVision Dual Link System-HRP, DAKO) was used as it was.

Immunohistochemical Staining

1. Deparaffinization, Peroxidase Blocking and Antigen Retrieval Treatment

These procedures were performed similarly as in Test Example 1.

2. Addition•Reaction of First Antibody or Negative Control (First Antibody Diluent)

Onto the slide glass from which an excess liquid was shaken off, a first antibody or a first antibody diluent was added dropwise to cause a reaction in a moist chamber at 25° C. for 30 minutes. Thereafter, the slide glass was washed in PBS for 3 minutes×twice. The combination of tissue and target marker binding molecule (first antibody) used in the study is as follows.

Gastric cancer . . . anti-human p53 gene product monoclonal antibody (DO-7) (NICHIREI BIOSCIENCES INC.) used as it was.

Colorectal cancer . . . anti-CDX-2 rabbit monoclonal antibody (NICHIREI BIOSCIENCES INC.) used as it was.

3. Reaction of First Binding Agent

Onto the slide glass from which an excess liquid was shaken off, EnVision Dual Link System-HRP (DAKO) was added dropwise to cause a reaction in a moist chamber at 25° C. for 10 minutes. Thereafter, the slide glass was washed in PBS for 3 minutes×twice. Incidentally, this reaction was carried out in Examples 6 and 7 and Comparative Examples 8 and 9.

4. Reaction with Linker Molecule

Onto the slide glass from which an excess liquid was shaken off, the mouse anti-HRP antibody (Example 6) or a rabbit anti-HRP antibody (Example 7) was added dropwise to cause a reaction in a moist chamber at 25° C. for 10 minutes. Thereafter, the slide glass was washed in PBS for 3 minutes×twice. Incidentally, this reaction was carried out in Examples 6 and 7 alone.

5. Reaction with Second Binding Agent

Onto the slide glass from which an excess liquid was shaken off, EnVision Dual Link System-HRP (DAKO) was added dropwise to cause a reaction in a moist chamber at 25° C. for 10 minutes. Thereafter, the slide glass was washed in PBS for 3 minutes×twice.

The reaction was carried out in Examples 6 and 7 and Comparative Example 9 alone.

6. Addition•Reaction of Substrate Solution

These procedures were performed similarly as in Test Example 1.

7. Counter Staining, Dehydration•Cleaning, Mounting

These procedures were performed similarly as in Test Example 1.

The results were as shown in FIG. 5. Here, the micrographs of the respective stained tissues shown in FIG. 5 were taken using an optical microscope (Olympus Corporation) with an ocular lens (10×) and an objective lens (4×).

Also when a dextran was used as the carrier and a whole antibody was used as the binding molecule, the reaction systems using the first binding agent, the linker molecule and the second binding agent (Examples 6 and 7) provided significantly improved detection sensitivity, as compared with the reaction system (Comparative Example 8) using the first binding agent alone and the reaction system (Comparative Example 9) using the first binding agent and the second binding agent alone.

Incidentally, no background staining occurred in the negative control.

4-2: Use of Direct Conjugate of Whole Antibody and HRP (First Binding Agent and Second Binding Agent)

Reagents comprising a whole IgG antibody and poly-HRP directly bound to each other were used as the first binding agent and the second binding agent to study the effect of detecting the target marker.

In the following experiment, a reaction system using the first binding agent (direct conjugate of an anti-mouse antibody and poly-HRP), the linker molecule (mouse anti-HRP antibody) and the second binding agent (direct conjugate of an anti-mouse antibody and poly-HRP) was defined as Example 8 (biological sample: p53 gastric cancer); and a reaction system using the first binding agent (direct conjugate of an anti-rabbit antibody and poly-HRP), the linker molecule (rabbit anti-HRP antibody) and the second binding agent (direct conjugate of an anti-rabbit antibody and poly-HRP) was defined as Example 9 (biological sample: CDX-2 colorectal cancer). Also, a reaction system using the first binding agent (direct conjugate of an anti-mouse antibody and poly-HRP) and the second binding agent (direct conjugate of an anti-mouse antibody and poly-HRP) alone was defined as Comparative Example 10 (biological sample: p53 gastric cancer); and a reaction system using the first binding agent (direct conjugate of an anti-rabbit antibody and poly-HRP) and the second binding agent (direct conjugate of an anti-rabbit antibody and poly-HRP) alone was defined as Comparative Example 11 (biological sample: CDX-2 colorectal cancer).

Reagent Preparation

1. Preparation of First Binding Agent

A reagent comprising a whole IgG antibody directly labeled with poly-HRP (Goat Anti-Mouse Poly-HRP, Pierce) was diluted 10-fold.

A reagent comprising a whole IgG antibody directly labeled with poly-HRP (Goat Anti-Rabbit Poly-HRP, Pierce) was diluted 10-fold.

2. Preparation of Linker Molecule

A mouse anti-HRP antibody (clone: HP-03, TFS) was prepared in 5 µg/mL.

A rabbit anti-HRP antibody (polyclonal) (NICHIREI BIOSCIENCES INC.) was prepared in 5 µg/mL.

3. Preparation of Second Binding Agent

The reagent comprising a whole IgG antibody directly labeled with poly-HRP (Goat Anti-Mouse Poly-HRP, Pierce) was diluted 10-fold.

The reagent comprising a whole IgG antibody directly labeled with poly-HRP (Goat Anti-Rabbit Poly-HRP, Pierce) was diluted 10-fold.

Immunohistochemical Staining

1. Deparaffinization, Peroxidase Blocking and Antigen Retrieval Treatment

These procedures were performed similarly as in Test Example 1.

2. Addition•Reaction of First Antibody or Negative Control (First Antibody Diluent)

These procedures were performed similarly as in Test Example 4-1.

3. Reaction with First Binding Agent

Onto the slide glass from which an excess liquid was shaken off, Goat Anti-Mouse Poly-HRP (Pierce) (Example 8 and Comparative Example 10) or Goat Anti-Rabbit Poly-HRP (Pierce) (Example 9 and Comparative Example 11) was added dropwise to cause a reaction in a moist chamber at 25° C. for 10 minutes. Thereafter, the slide glass was washed in PBS for 3 minutes×twice. Incidentally, this reaction was carried out in Examples 8 and 9 and Comparative Examples 10 and 11.

4. Reaction with Linker Molecule

Onto the slide glass from which an excess liquid was shaken off, the mouse anti-HRP antibody (Example 8) or the rabbit anti-HRP antibody (Example 9) was added dropwise to cause a reaction in a moist chamber at 25° C. for 10 minutes. Thereafter, the slide glass was washed in PBS for 3 minutes×twice. Incidentally, this reaction was carried out in Examples 8 and 9.

5. Reaction with Second Binding Agent

Onto the slide glass from which an excess liquid was shaken off, Goat Anti-Mouse Poly-HRP (Pierce) (Example 8 and Comparative Example 10) or Goat Anti-Rabbit Poly-HRP (Pierce) (Example 9 and Comparative Example 11) was added dropwise to cause a reaction in a moist chamber at 25° C. for 10 minutes. Thereafter, the slide glass was washed in PBS for 3 minutes×twice. Incidentally, this reaction was carried out in Examples 8 and 9 and Comparative Examples 10 and 11.

6. Addition•Reaction of Substrate Solution

These procedures were performed similarly as in Test Example 1.

7. Counter Staining, Dehydration•Cleaning, Mounting

These procedures were performed similarly as in Test Example 1.

The results were as shown in FIG. 6. Here, the micrographs of the respective stained tissues shown in FIG. 6 were taken using an optical microscope (Olympus Corporation) with an ocular lens (10×) and an objective lens (4×).

Also when direct conjugates of a whole antibody and a labeling substance (poly-HRP) were used as the first binding agent and the second binding agent, the reaction systems (Examples 8 and 9) using the first binding agent, the linker molecule and the second binding agent each provided significantly improved detection sensitivity, as compared with the reaction systems (Comparative Examples 10 and 11) using the first binding agent and the second binding agent alone.

Incidentally, background staining occurred in the negative controls of Examples 8 and 9, but mainly occurred in the cytoplasm and hardly occurred in the cell nucleus. The p53 and CDX-2 antibodies stain the cell nucleus, and thus were hardly affected by background staining at the time of evaluation.

4-3: Use of Enzyme Micropolymers (First Binding Agent and Second Binding Agent)

Enzyme micropolymers comprising enzymes with high activity and high density and an antibody bound to each other (ImmPRESS UNIVERSAL Reagent, Anti-Mouse/Rabbit Ig or ImmPRESS Reagent, Anti-Goat Ig; VECTOR LABORATORIES) were used as the first binding agent and the second binding agent for a comparative test on staining sensitivity in accordance with the following procedures.

Incidentally, a reaction system using the first binding agent (ImmPRESS UNIVERSAL Reagent, Anti-Mouse/Rabbit Ig), the linker molecule (mouse anti-HRP antibody) and the second binding agent (ImmPRESS UNIVERSAL Reagent, Anti-Mouse/Rabbit Ig) was defined as Example 10; a reaction system using the first binding agent (ImmPRESS UNIVERSAL Reagent, Anti-Mouse/Rabbit Ig), the linker molecule (rabbit anti-HRP antibody) and the second binding agent (ImmPRESS UNIVERSAL Reagent, Anti-Mouse/Rabbit Ig) was defined as Example 11; and a reaction system using the first binding agent (ImmPRESS UNIVERSAL Reagent, Anti-Mouse/Rabbit Ig), the linker molecule (goat anti-HRP antibody) and the second binding agent (ImmPRESS Reagent, Anti-Goat Ig) was defined as Example 12.

Also, a reaction system using the first binding agent (ImmPRESS UNIVERSAL Reagent, Anti-Mouse/Rabbit Ig) alone was defined as Comparative Example 12; a reaction system using the first binding agent (ImmPRESS UNIVERSAL Reagent, Anti-Mouse/Rabbit Ig) and the second binding agent (ImmPRESS UNIVERSAL Reagent, Anti-Mouse/Rabbit Ig) alone was defined as Comparative Example 13; and a reaction system using the first binding agent (ImmPRESS UNIVERSAL Reagent, Anti-Mouse/Rabbit Ig) and the second binding agent (ImmPRESS Reagent, Anti-Goat Ig) alone was defined as Comparative Example 14.

Reagent Preparation

1. Preparation of First Binding Agent

Enzyme micropolymers comprising enzymes with high activity and high density and an antibody bound to each other (ImmPRESS UNIVERSAL Reagent, Anti-Mouse/Rabbit Ig, VECTOR LABORATORIES) was used as it was.

2. Preparation of Linker Molecule

A mouse anti-HRP antibody (clone: HP-03, TFS) was prepared in 5 µg/mL.

A rabbit anti-HRP antibody (polyclonal) (NICHIREI BIOSCIENCES INC.) was prepared in 5 µg/mL.

A goat anti-HRP antibody (polyclonal) (Pierce) was prepared in 5 µg/mL.

3. Preparation of Second Binding Agent

Enzyme micropolymers comprising enzymes with high activity and high density and an antibody bound to each other (ImmPRESS UNIVERSAL Reagent, Anti-Mouse/Rabbit Ig, VECTOR LABORATORIES) was used as it was.

Also, another enzyme micropolymers comprising enzymes with high activity and high density and an antibody bound to each other (ImmPRESS Reagent, Anti-Goat Ig, VECTOR LABORATORIES) was used as it was.

Immunohistochemical Staining

1. Deparaffinization, Peroxidase Blocking and Antigen Retrieval Treatment

These procedures were performed similarly as in Test Example 1.

2. Addition•Reaction of First Antibody or Negative Control (First Antibody Diluent)

These procedures were performed similarly as in Test Example 4-1.

3. Reaction with First Binding Agent

Onto the slide glass from which an excess liquid was shaken off, ImmPRESS UNIVERSAL Reagent, Anti-Mouse/Rabbit Ig (VECTOR LABORATORIES) was added dropwise to cause a reaction in a moist chamber at 25° C. for 10 minutes. Thereafter, the slide glass was washed in PBS for 3 minutes×twice. Incidentally, this reaction was carried out in Examples 10 to 12 and Comparative Examples 12 to 14.

4. Reaction with Linker Molecule

Onto the slide glass from which an excess liquid was shaken off, the mouse anti-HRP antibody (Example 10), the rabbit anti-HRP antibody (Example 11) or the goat anti-HRP antibody (Example 12) was added dropwise to cause a reaction in a moist chamber at 25° C. for 10 minutes. Thereafter, the slide glass was washed in PBS for 3 minutes× twice. Incidentally, this reaction was carried out in Examples 10 to 12 alone.

5. Reaction with Second Binding Agent

Onto the slide glass from which an excess liquid was shaken off, ImmPRESS UNIVERSAL Reagent, Anti-Mouse/Rabbit Ig (VECTOR LABORATORIES) (Examples 10 and 11 and Comparative Example 13) or ImmPRESS Reagent, Anti-Goat Ig (VECTOR LABORATORIES) (Example 12 and Comparative Example 14) was added dropwise to cause a reaction in a moist chamber at 25° C. for 10 minutes. Thereafter, the slide glass was washed in PBS for 3 minutes×twice. Incidentally, this reaction was carried out in Examples 10 to 12 and Comparative Examples 13 and 14.

6. Addition•Reaction of Substrate Solution

These procedures were performed similarly as in Test Example 1.

7. Counter Staining, Dehydration•Cleaning, Mounting

These procedures were performed similarly as in Test Example 1.

The results were as shown in FIG. 7. Here, the micrographs of the respective stained tissues shown in FIG. 7 were taken using an optical microscope (Olympus Corporation) with an ocular lens (10×) and an objective lens (4×).

Also when enzyme micropolymers comprising enzymes with high activity and high density and an antibody bound to each other were used as the first binding agent and the second binding agent, the reaction systems (Examples 10 to 12) using the first binding agent, the linker molecule and the second binding agent each provided significantly improved detection sensitivity, as compared with the reaction system (Comparative Example 12) using the first binding agent alone and the reaction systems (Comparative Examples 13 and 14) using the first binding agent and the second binding agent alone.

Incidentally, background staining occurred in the negative control of Examples 10 to 12, but mainly occurred in the cytoplasm and hardly occurred in the cell nucleus. The p53 and CDX-2 antibodies are stained in the cell nucleus, and thus were hardly affected by background staining at the time of evaluation.

Test Example 5: Study of Presence or Absence of Polymer Carriers in First Binding Agent and Second Binding Agent and Molecular Weights of Polymer Carriers As indicated in the following Tables 2 to 5, polymer reagents comprising polymer carriers varying in molecular weight or a reagent of poly-HRP type having no polymer carrier were selected as the first binding agent and the second binding agent. A similar test as in Test Example 2 was conducted for comparison of the detection sensitivity for the target marker, except that a gastric cancer tissue alone was used as a biological sample, and that the target marker binding molecule (first antibody: anti-human p53 gene product monoclonal antibody (DO-7) (NICHIREI BIOSCIENCES INC.)) was used diluted 2-fold.

TABLE 2

|  | Comparative Example 15 | Comparative Example 16 | Example 13 |
|---|---|---|---|
| First binding agent | Polymer reagent (M) (molecular weight: 2,700) | Polymer reagent (M) (molecular weight: 2,700) | Polymer reagent (M) (molecular weight: 2,700) |
| Linker molecule | None | None | Mouse anti-HRP antibody |
| Second binding agent | None | Polymer reagent (M) (molecular weight: 2,700) | Polymer reagent (M) (molecular weight: 2,700) |

TABLE 3

|  | Comparative Example 17 | Comparative Example 18 | Example 14 |
|---|---|---|---|
| First binding agent | Polymer reagent (M) (molecular weight: 7,500) | Polymer reagent (M) (molecular weight: 7,500) | Polymer reagent (M) (molecular weight: 7,500) |
| Linker molecule | None | None | Mouse anti-HRP antibody |
| Second binding agent | None | Polymer reagent (M) (molecular weight: 7,500) | Polymer reagent (M) (molecular weight: 7,500) |

TABLE 4

|  | Comparative Example 19 | Comparative Example 20 | Example 15 |
|---|---|---|---|
| First binding agent | Polymer reagent (M) (molecular weight: 9,200) | Polymer reagent (M) (molecular weight: 9,200) | Polymer reagent (M) (molecular weight: 9,200) |
| Linker molecule | None | None | Mouse anti-HRP antibody |
| Second binding agent | None | Polymer reagent (M) (molecular weight: 9,200) | Polymer reagent (M) (molecular weight: 9,200) |

TABLE 5

|  | Comparative Example 21 | Comparative Example 22 | Example 16 |
|---|---|---|---|
| First binding agent | Poly-HRP type reagent (M) (no polymer carrier) | Poly-HRP type reagent (M) (no polymer carrier) | Poly-HRP type reagent (M) (no polymer carrier) |
| Linker molecule | None | None | Mouse anti-HRP antibody |
| Second binding agent | None | Poly-HRP type reagent (M) (no polymer carrier) | Poly-HRP type reagent (M) (no polymer carrier) |

Reagent Preparation

1. Preparation of First Binding Agent

The first binding agents (polymer reagents) were produced in accordance with the descriptions in paragraphs [0031] to [0040] of JP 2001-181299 A.

Specifically, the polymer reagents were produced similarly to the polymer reagent (M) in Test Example 1, except that the average molecular weights of the polymer carriers were defined as 2,700, 7,500 and 9,200, respectively. The polymer reagents were prepared in 5 µg/mL. Incidentally, the polymer carrier of the polymer reagent (M) used in Test Example 1 has an average molecular weight of 9,200.

Also, as regards the reagent of poly-HRP type having no polymer carrier, the reagent (M) comprising Fab' of anti-mouse Ig (animal species: goat) and poly-HRP bound thereto was prepared in 5 µg/mL.

2. Preparation of Linker Molecule

A mouse anti-HRP antibody (clone: HP-03, TFS) was prepared in 5 µg/mL.

3. Preparation of Second Binding Agent

The above first binding agents were prepared in 7.5 µg/mL.

The results were as shown in FIG. 8. Here, the micrographs of the respective stained tissues shown in FIG. 8 were taken using an optical microscope (Olympus Corporation) with an ocular lens (10×) and an objective lens (4×).

Example 13 to 16 using the linker molecule were each confirmed to provide significantly improved detection sensitivity, regardless of the differences in molecular weights in the first binding agent and the second binding agent or the presence or absence of the polymer carrier (poly-L-lysine (PLL)), as compared with Comparative Examples 15 to 22 using no linker molecule. Incidentally, no background staining occurred in the negative control.

Test Example 6: Study of Labeling Substance 6-1: Reaction System Using Labeling Substance (Alkaline Phosphatase: AP) and Linker Molecule (Mouse Anti-AP Antibody)

A reaction system using alkaline phosphatase (AP), in place of horseradish peroxidase (HRP), as the labeling substance and the linker molecule (mouse anti-AP antibody) was studied in terms of detection sensitivity for the target marker.

Incidentally, in the following test, a reaction system using the first binding agent and the second binding agent (amino acid polymer using alkaline phosphatase (AP) as the labeling substance: AP polymer reagent (M)) and the linker molecule (mouse anti-AP antibody) was defined as Example 17; a reaction system using the first binding agent (AP polymer reagent (M)) alone was defined as Comparative Example 23; and a reaction system using the first binding agent and the second binding agent (AP polymer reagent (M)) alone was defined as Comparative Example 24.

Reagent Preparation

1. Preparation of First Binding Agent

An AP polymer reagent (M) comprising alkaline phosphatases (AP) and Fab' fragments of anti-mouse Ig (animal species: goat) bound to an amino acid polymer was prepared in 10 µg/mL.

2. Preparation of Linker Molecule

A mouse anti-AP antibody (clone: AP1B9, NOVUS BIOLOGICALS, LLC) was prepared in 5 µg/mL.

3. Preparation of Second Binding Agent

The AP polymer reagent (M) (NICHIREI BIOSCIENCES INC.) was prepared in 10 µg/mL.

Immunohistochemical Staining
1. Deparaffinization, Peroxidase Blocking and Antigen Retrieval Treatment These procedures were performed similarly as in Test Example 1.

2. Addition•Reaction of First Antibody or Negative Control (First Antibody Diluent)

Onto the slide glass from which an excess liquid was shaken off, a first antibody or a first antibody diluent was added dropwise to cause a reaction in a moist chamber at 25° C. for 30 minutes. Thereafter, the slide glass was washed in PBS for 3 minutes×twice. The combination of tissue and first antibody used in the study is as follows.

Gastric cancer . . . anti-human p53 gene product monoclonal antibody (DO-7) (NICHIREI BIOSCIENCES INC.) used as it was.

3. Reaction with First Binding Agent

Onto the slide glass from which an excess liquid was shaken off, the AP polymer reagent (M) was added dropwise to cause a reaction in a moist chamber at 25° C. for 10 minutes. Thereafter, the slide glass was washed in PBS for 3 minutes×twice. Incidentally, this reaction was carried out in Example 17 and Comparative Examples 23 and 24.

4. Reaction with Linker Molecule

Onto the slide glass from which an excess liquid was shaken off, the mouse anti-AP antibody was added dropwise to cause a reaction in a moist chamber at 25° C. for 10 minutes. Thereafter, the slide glass was washed in PBS for 3 minutes×twice. Incidentally, this reaction was carried out in Example 17 alone.

5. Reaction with Second Binding Agent

Onto the slide glass from which an excess liquid was shaken off, the AP polymer reagent (M) was added dropwise to cause a reaction in a moist chamber at 25° C. for 10 minutes. Thereafter, the slide glass was washed in PBS for 3 minutes×twice. Incidentally, this reaction was carried out in Example 17 and Comparative Example 24 alone.

6. Addition•Reaction of Substrate Solution

Onto the slide glass from which an excess liquid was shaken off, Fast-Red II Substrate Kit (NICHIREI BIOSCIENCES INC.) was added dropwise to cause a reaction at room temperature for 10 minutes. Thereafter, the slide glass was washed with running water for 5 minutes.

7. Counter Staining, Dehydration•Cleaning, Mounting

A. Counter Staining

After drained, the slide glass was immersed in a Mayer's hematoxylin solution for 30 seconds. Thereafter, the slide glass was washed with running water for 5 minutes.

B. Air-Drying

After drained, air-drying was carried out by using a dryer.

C. Mounting

The slide glass was slightly immersed in xylene, and, thereafter, Permanent Mounting Media (Non-Aqueous) (NICHIREI BIOSCIENCES INC.) was used for mounting.

The results were as shown in FIG. 9. Here, the micrographs of the respective stained tissues shown in FIG. 9 were taken using an optical microscope (Olympus Corporation) with an ocular lens (10×) and an objective lens (4×).

When alkaline phosphatase (AP) was used as the labeling substance, Example 17 using the first binding agent, the linker molecule and the second binding agent provided significantly improved detection sensitivity, as compared with Comparative Example 23 using the first binding agent alone and Comparative Example 24 using the first binding agent and the second binding agent alone.

Incidentally, no background staining occurred in the negative control.

Test Example 6-2: Reaction System Using Labeling Substance (Alkaline Phosphatase: AP) and Linker Molecule (Rabbit Anti-AP Antibody)

A reaction system using alkaline phosphatase (AP), in place of horseradish peroxidase (HRP), as the labeling substance and the linker molecule (rabbit anti-AP antibody) was studied in terms of detection sensitivity for the target marker.

In the following test, a reaction system using the first binding agent and the second binding agent (amino acid polymer using alkaline phosphatase (AP) as the labeling substance: AP polymer reagent (R)) and the linker molecule (rabbit anti-AP antibody) was defined as Example 18; a reaction system using the first binding agent (AP polymer reagent (R)) alone was defined as Comparative Example 25; and a reaction system using the first binding agent and the second binding agent (AP polymer reagent (R)) alone was defined as Comparative Example 26.

Reagent Preparation
1. Preparation of First Binding Agent

An AP polymer reagent (R) comprising alkaline phosphatases (AP) and Fab' fragments of anti-rabbit Ig (animal species: goat) bound to an amino acid polymer was prepared in 10 μg/mL.

2. Preparation of Linker Molecule

A rabbit anti-AP antibody (polyclonal, NOVUS BIOLOGICALS, LLC) was prepared in 5 μg/mL.

3. Preparation of Second Binding Agent

The AP polymer reagent (R) was prepared in 10 μg/mL.

Immunohistochemical Staining
1. Deparaffinization, Peroxidase Blocking and Antigen Retrieval Treatment These procedures were performed similarly as in Test Example 1.

2. Addition•Reaction of First Antibody or Negative Control (First Antibody Diluent)

Onto the slide glass from which an excess liquid was shaken off, a first antibody or a first antibody diluent was added dropwise to cause a reaction in a moist chamber at 25° C. for 30 minutes. Thereafter, the slide glass was washed in PBS for 3 minutes×twice. The combination of tissue and first antibody used in the study is as follows.

Colorectal cancer . . . anti-CDX-2 rabbit monoclonal antibody (NICHIREI BIOSCIENCES INC.) used as it was.

3. Reaction with First Binding Agent

Onto the slide glass from which an excess liquid was shaken off, the AP polymer reagent (R) was added dropwise to cause a reaction in a moist chamber at 25° C. for 10 minutes. Thereafter, the slide glass was washed in PBS for 3 minutes×twice. Incidentally, this reaction was carried out in Example 18 and Comparative Examples 25 and 26.

4. Reaction with Linker Molecule

Onto the slide glass from which an excess liquid was shaken off, the rabbit anti-AP antibody was added dropwise to cause a reaction in a moist chamber at 25° C. for 10 minutes. Thereafter, the slide glass was washed in PBS for 3 minutes×twice. Incidentally, this reaction was carried out in Example 18 alone.

5. Reaction with Second Binding Agent

Onto the slide glass from which an excess liquid was shaken off, the AP polymer reagent (R) was added dropwise to cause a reaction in a moist chamber at 25° C. for 10 minutes. Thereafter, the slide glass was washed in PBS for 3 minutes×twice. Incidentally, this reaction was carried out in Example 18 and Comparative Example 26 alone.

6. Addition•Reaction of Substrate Solution

Onto the slide glass from which an excess liquid was shaken off, Fast-Red II Substrate Kit (NICHIREI BIOSCIENCES INC.) was added dropwise to cause a reaction at room temperature for 10 minutes. Thereafter, the slide glass was washed with running water for 5 minutes.

7. Counter Staining, Dehydration•Cleaning, Mounting

These procedures were performed similarly as in Test Example 6-1.

The results were as shown in FIG. 10. Here, the micrographs of the respective stained tissues shown in FIG. 10 were taken using an optical microscope (Olympus Corporation) with an ocular lens (10×) and an objective lens (4×).

When alkaline phosphatase (AP) was used as the labeling substance, Example 18 using the first binding agent, the linker molecule and the second binding agent provided significantly improved detection sensitivity, as compared with Comparative Example 25 using the first binding agent alone and Comparative Example 26 using the first binding agent and the second binding agent alone.

Incidentally, no background staining occurred in the negative control.

Test Example 7: Study of High-Sensitivity Staining Method by CISH Method

In this test, it was reviewed, in accordance with the following procedures, whether the present invention could be applied to the CISH method (Chromogenic in situ Hybridization: in situ Hybridization (ISH) involving detecting DNA and mRNA on a tissue specimen using a dye such as 3,3'-diaminobenzidine (DAB)). A probe labeled with digoxigenin (DIG) was applied, as the target marker binding molecule, to a tissue specimen. After blocking, the probe was detected using a detection reagent capable of directly binding to DIG.

In this test, HER2 Probe was used as the target marker binding molecule.

Then, in Example 19, a reaction system using the first binding agent (goat anti-DIG-HRP polymer reagent (NICHIREI BIOSCIENCES INC.)), the linker molecule (rabbit anti-HRP antibody (polyclonal)) (NICHIREI BIOSCIENCES INC.)) and the second binding agent (Histofine® Simple Stain® MAX-PO (R), (NICHIREI BIOSCIENCES INC.)) as the detection reagent was selected.

Also, in Comparative Example 27, a reaction system using the first binding agent (goat anti-DIG-HRP polymer reagent) alone was selected as the detection reagent. Further, in Comparative Example 28, a reaction system using the first binding agent (goat anti-DIG antibody) and the second binding agent (Histofine® Simple Stain® MAX-PO (G) (NICHIREI BIOSCIENCES INC.)) as the detection reagent was selected.

CISH

1. Deparaffinization, Peroxidase Blocking and Antigen Retrieval Treatment. Dehydration•Air-Drying A. Provision of Specimen Slide A tissue section was sliced into 5 μm and mounted onto a MAS-coated slide glass. Thereafter, the slide glass was dried overnight in an incubator at 37° C.

B. Deparaffinization, Peroxidase Blocking and Antigen Retrieval Treatment, Dehydration•Air-Drying (I) Xylene Treatment (3 Minutes×3 Times)

The slide was immersed in xylene for 3 minutes. Thereafter, an excess liquid was shaken off, and then the slide was immersed in another xylene for 3 minutes. Thereafter, an excess liquid was shaken off, and the slide was immersed in still another xylene for 3 minutes.

(II) Ethanol Treatment (3 Minutes×4 Times)

The slide was Immersed in 100% ethanol for 3 minutes. An excess liquid was shaken off, and the slide was immersed in another 100% ethanol for 3 minutes. This operation was carried out twice more.

(III) Peroxidase Blocking

Endogenous peroxidase was blocked. After drained, the slide was Immersed in a 3V/V % hydrogen peroxide solution for 5 minutes (IV) Washing The slide was washed in PBS (twice, respectively for 1 minute).

(V) Antigen Retrieval Treatment

As pretreatment, an antigen retrieval solution (10 mM sodium citrate buffer (pH 6.0)) was used for heating treatment at 98° C. for 30 minutes.

(VI) Washing

The slide was washed in PBS (twice, respectively for 2 minutes).

(VII) Antigen Retrieval Treatment

Protease treatment was carried out in a moist chamber at room temperature for 3 minutes.

(VIII) Washing

The slide was washed in PBS.

(IX) Dehydration

The slide was immersed in 70% ethanol, 90% ethanol and 100% ethanol, respectively, for 1 minute, and then air-dried.

Denaturation and Hybridization (I) HER2 Probe was vortexed, and applied to a slide.

(II) A cover glass was placed on the slide while avoiding bubbles, and sealed on its periphery with a paper bond.

(III) A hot plate was used for denaturation at 82° C. for 5 minutes.

(IV) The slide was moved into the moist chamber for hybridization at 37° C. overnight.

Post-Hybridization and Detection (I) After careful peeling of the paper bond, the slide was washed in 2×SSC at room temperature for 5 minutes. Then, the cover glass was removed.

(II) The slide was washed in 2×SSC at 72° C. for 5 minutes.

(III) The slide was washed in PBS twice, respectively for 1 minute.

(IV) As indicated in Table 6, reactions were carried out for Example 19 and Comparative Examples 27 and 28. Here, all the reactions were carried out at 25° C. Between the respective steps, the slide was washed in PBS three times, respectively for 1 minute.

TABLE 6

|  | Comparative Example 27 | | Comparative Example 28 | | Example 19 | |
| --- | --- | --- | --- | --- | --- | --- |
|  | Reaction reagent | Reaction time | Reaction reagent | Reaction time | Reaction reagent | Reaction time |
| First binding agent | Goat anti-DIG-HRP polymer | 30 minutes | Goat anti-DIG antibody | 15 minutes | Goat anti-DIG-HRP polymer | 15 minutes |
| Linker agent | None | | None | | Rabbit anti-HRP antibody | 15 minutes |
| Second binding agent | None | | MAX-PO (G) | 15 minutes | MAX-PO (R) | 15 minutes |

(V) The slide was washed in PBS three times, respectively for 1 minute. Thereafter, PBS was drained well.

(VI) Onto the slide glass from which an excess liquid was shaken off, N-Histofine® DAB-2V (NICHIREI BIOSCIENCES INC.) was added dropwise to cause a reaction at room temperature for 5 minutes.

(VII) The slide glass was washed with running water for 5 minutes.

(VIII) After drained, the slide glass was immersed in a Mayer's hematoxylin solution for 15 seconds for counter staining.

(IX) The slide glass was washed with running water for 5 minutes.

(x) Draining was followed by dehydration with 100% ethanol for 3 minutes.

(XI) The slide was cleared with xylene twice, respectively for 5 minutes.

(XII) Permanent Mounting Media (Non-Aqueous) (NICHIREI BIOSCIENCES INC.) was used for mounting.

The staining Intensity by CISH was visually determined, based on the signal of Comparative Example 27 defined as 1+, using an optical microscope (Olympus Corporation) (with an ocular lens (10×) and an objective lens (×100)), and, as a result, was as indicated in the following Table 7. Example 19 provided significantly improved detection sensitivity, as compared with Comparative Examples 27 and 28.

TABLE 7

|  | Comparative Example 27 | Comparative Example 28 | Example 19 |
| --- | --- | --- | --- |
| Signal | 1+ | 1.5+ | 3+ |
| Background staining | None | None | None |

Test Example 8: Study of Enhancement of Immunoreaction Use of Polyethylene Glycol A comparative test was conducted in order to review how the detection sensitivity for the target marker varied when any of the three-stage immunoreactions of the present invention was carried out in the coexistence of polyethylene glycol.

Specifically, in Example 20, the three-stage immunoreactions were carried out using the first binding agent, the linker molecule and the second binding agent, without coexistence of polyethylene glycol.

In Example 21, the first-stage immunoreaction was carried out in the coexistence of polyethylene glycol and the first binding agent, and then the second- and third-stage immunoreactions were respectively conducted using the linker molecule and the second binding agent.

In Example 23, the first-stage immunoreaction was carried out using the first binding agent; the second-stage immunoreaction was carried out in the coexistence of polyethylene glycol and the linker molecule; and, then, the third-stage Immunoreaction was carried out using the second binding agent.

In Example 22, the first-stage immunoreaction was carried out using the first binding agent; the second-stage immunoreaction was carried out using the linker molecule; and, then, the third-stage immunoreaction was carried out in the coexistence of polyethylene glycol and the second binding agent.

In Example 24, all the three-stage Immunoreactions using the first binding agent, the linker molecule and the second binding agent were conducted in the coexistence of polyethylene glycol.

Incidentally, specific procedures were performed in accordance with Test Example 2, except that a colorectal cancer tissue alone was used as a biological sample, and that the target marker binding molecule (first antibody: anti-CDX-2 rabbit monoclonal antibody (NICHIREI BIOSCIENCES INC.)) was diluted 5-fold.

Reagent Preparation

1. Preparation of First Binding Agent

A polymer reagent (M) comprising peroxidases and Fab' fragments of anti-mouse Ig (animal species: goat) bound to an amino acid polymer and a polymer reagent (R) comprising peroxidases and Fab' fragments of anti-rabbit Ig (animal species: goat) bound to an amino acid polymer were mixed in each amount of 5 µg/mL, thereby preparing a cocktail polymer reagent (MULTI).

2. Preparation of Linker Molecule

A mouse anti-HRP antibody (clone: HP-03) (TFS) and a mouse anti-HRP antibody (clone: 2H11) (Novus Biologicals, LLC) were mixed in each amount of 2.5 µg/mL, thereby preparing a linker molecule.

3. Preparation of Second Binding Agent

The polymer reagent (M) comprising peroxidases and Fab' fragments of anti-mouse Ig (animal species: goat) bound to an amino acid polymer was prepared in 5 µg/mL.

4. Polyethylene Glycol

In Examples 21 to 24, polyethylene glycol (average molecular weight (MW): 8,000, Wako Pure Chemical Industries, Ltd.) was dissolved, in an amount of 2.5 wt %, in any of aqueous solutions constituting the first binding agent, the linker molecule and the second binding agent.

The results were as shown in FIG. 11. Here, the micrographs of the respective stained tissues shown in FIG. 11 were taken using an optical microscope (Olympus Corporation) with an ocular lens (10×) and an objective lens (4×).

Examples 21 to 24 with coexistence of polyethylene glycol in any of the immunoreactions provided improved detection sensitivity, as compared with Example 20 without coexistence of polyethylene glycol in any of the immunoreactions. Especially, Example 24 with coexistence of polyethylene glycol in all the stages (first to third stages) provided significantly improved detection sensitivity, as compared with Example 20.

The invention claimed is:

1. A combination product for detecting a target marker in a biological sample in combination with a target marker binding molecule which is capable of binding specifically to the target marker, the combination product comprising, at least:
   (a) a first binding agent comprising a first antibody or an antigen binding fragment thereof, and a labeling substance, wherein the first antibody or antigen binding fragment thereof is capable of directly or indirectly binding specifically to the target marker binding molecule and wherein the antibody or antigen binding fragment thereof is connected with the labeling substance directly or indirectly via a carrier,
   (b) a second binding agent comprising a second antibody or an antigen binding fragment thereof and the labeling substance, wherein the second antibody or an antigen binding fragment thereof is capable of binding specifically to the linker molecule, wherein the antibody or the antigen binding fragment thereof is connected with the labeling substance directly or indirectly via a carrier; and
   (c) a linker molecule, wherein the linker molecule is a non-labelled antibody or non-labeled antigen binding fragment thereof, capable of binding specifically to the labeling substance in the first binding agent and the labeling substance in the second binding agent, and wherein the binding sites between the linker molecule and the second binding agent comprise at least two binding sites which contain a binding site via the second antibody or antigen binding fragment thereof and a binding site via the labeling substance,
   wherein the carrier of the first binding agent of (a) and the carrier of the second binding agent of (b) is a polymer having an average molecular weight of within the range of 2,000 to 500,000.

2. The combination product according to claim 1, wherein the labeling substance is at least one selected from a chemiluminescent label, a metal particle, a fluorescent label, an enzyme label, a coenzyme label, a labeled antibody, a dye, a bioluminescent label, a hapten and a polymer particle.

3. The combination product according to claim 1, further comprising the target marker binding molecule.

4. A kit comprising the combination product according to claim 1.

* * * * *